(12) United States Patent
Hsu et al.

(10) Patent No.: US 9,384,651 B2
(45) Date of Patent: Jul. 5, 2016

(54) CLINICAL INFORMATION MANAGEMENT SYSTEM

(71) Applicant: MedicusTek Inc., Taipei (TW)

(72) Inventors: Chia-Ming Hsu, Taipei (TW); Ling-Hsuan Liu, Taipei (TW); Shih-Ju Wang, Taipei (TW); Lavina Che-Hsuan Thong, Taipei (TW); Han-Wen Tso, Taipei (TW); Sung-Ho Huang, Taipei (TW); Mark Daniel Anderson, Taipei (TW)

(73) Assignee: MedicusTek Inc., Taipei (TW)

( * ) Notice: Subject to any disclaimer, the term of this patent is extended or adjusted under 35 U.S.C. 154(b) by 0 days.

(21) Appl. No.: 14/315,329

(22) Filed: Jun. 26, 2014

(65) Prior Publication Data
US 2015/0170494 A1   Jun. 18, 2015

(30) Foreign Application Priority Data

Dec. 18, 2013   (TW) .............................. 102146970 A

(51) Int. Cl.
*G08B 1/08*   (2006.01)
*G08B 21/22*   (2006.01)
*G06F 19/00*   (2011.01)

(52) U.S. Cl.
CPC ............ *G08B 21/22* (2013.01); *G06F 19/3418* (2013.01); *G06F 19/345* (2013.01); *G06F 19/3487* (2013.01)

(58) Field of Classification Search
CPC .............. A61B 5/1115; A61B 5/6891; A61B 2562/029; A61B 19/5202; A61B 2562/0252; A61B 5/0205; A61B 5/1113; A61B 5/1128; A61B 5/6889; A61B 5/7275; A61B 5/743; A61B 5/7475; A61B 7/00; A61B 2562/0247

USPC ........... 340/539.17, 556, 286.07, 521, 573.1, 340/573.7, 539.12, 539.11, 666, 665, 340/603–604
See application file for complete search history.

(56) References Cited

U.S. PATENT DOCUMENTS 5,005,240 A * 4/1991 Vrzalik ................ A61G 7/0506
   137/596.17
5,600,305 A * 2/1997 Stafford ............... A61B 5/1104
   340/556

(Continued)

FOREIGN PATENT DOCUMENTS

TW        201337825 A    9/2013

OTHER PUBLICATIONS

Office Action issued in corresponding Taiwanese Application No. 102146970 dated Oct. 22, 2015 (12 pages).

*Primary Examiner* — Daniel Previl
(74) *Attorney, Agent, or Firm* — Osha Liang LLP

(57) ABSTRACT

Disclosed herein is a clinical information management system that includes a nurses station server, a plurality of pressure sensing pads, a wireless router, a system terminal equipment and a mobile device. The sensing pads are distributed to beds, and each sensing pad is connected to a wireless control box. The wireless router receives a pressure-sensing signal from the wireless control box and transmits the pressure-sensing signal to the nurses station server. The system terminal equipment is connected with the nurses station server via the Internet and receives the pressure-sensing signal transmitted from the nurses station server. The mobile device receives the pressure-sensing signal from the nurses station server or the system terminal equipment.

31 Claims, 11 Drawing Sheets

(56) References Cited

U.S. PATENT DOCUMENTS

| | | | | |
|---|---|---|---|---|
| 5,699,038 A | * | 12/1997 | Ulrich | A61G 12/00 340/286.06 |
| 2005/0110617 A1 | * | 5/2005 | Kile | G08B 21/22 340/286.07 |
| 2009/0289800 A1 | * | 11/2009 | Hansen | A61B 5/1115 340/573.1 |
| 2010/0045454 A1 | * | 2/2010 | Knight | G08B 21/0469 340/521 |
| 2010/0163315 A1 | * | 7/2010 | York | G01G 19/44 177/144 |
| 2010/0212087 A1 | * | 8/2010 | Leib | G06F 19/327 5/81.1 R |
| 2013/0174345 A1 | | 7/2013 | Leu et al. | |
| 2014/0068860 A1 | * | 3/2014 | Shih | A61B 5/1115 5/600 |

\* cited by examiner

CLINICAL INFORMATION MANAGEMENT SYSTEM

This application claims priority to the Taiwanese Application Serial Number 102146970, filed Dec. 18, 2013, which is incorporated herein by reference.

BACKGROUND

1. Field of Invention

The present invention relates to a management system. Specifically, the present invention relates to a clinical information management system.

2. Description of Related Art

Nurses stations are areas in a health care facility (such as a hospital or nursing home) where nurses centralize patient monitoring and ward administration. Nurses stations are often located at the center of wards, near patient rooms, so as to facilitate the ward administration and allow patients, accompanying families and visitors to receive assistance from nurses. In some hospitals, the nurses station is a closed-type space that is similar to an office, while in other hospitals, the nurses station may be an open-type space such as a counter with a semicircular, waist-high work bench. Often, nurses stations have a physical white board for manually recording patient status and test results as well as recording the medical attendants' schedule and notices related to the patients in order to constantly display and remind patient requirements. However, one disadvantage of the physical white board is that it cannot update information in real-time. This information includes details about the patient position and motion while in bed or seated in a chair, which is important for reducing patient falls and pressure ulcers.

In view of the foregoing, the existing problem and disadvantage in the current related art is in need of further improvement; however, those skilled in the art have sought vainly for a suitable solution for remotely monitoring patient position and motion and updating patients' physiological information in real-time. In order to solve such problem and disadvantage, there is an urgent need in the related field to provide a means for remotely monitoring patient position and motion and updating patients' physiological information in real-time.

SUMMARY

The following presents a simplified summary of the disclosure in order to provide a basic understanding to the reader. This summary is not an extensive overview of the disclosure and does not identify key/critical components or delineate the scope of the present invention. Its sole purpose is to present some concepts disclosed herein in a simplified form as a prelude to the more detailed description that is presented later.

The present disclosure provides a clinical information management system and a method for managing hospital beds to solve the aforesaid problems and disadvantages.

The clinical information management system according to the present disclosure comprises a nurses station server, one or more pressure sensing pads, and one or more wireless control boxes. Additionally, the clinical information management system may include a wireless router, system terminal equipment and one or more mobile devices. The one or more pressure sensing pads are distributed to one or more beds, and each pressure sensing pad is configured to generate an electrical signal in response to the presence and motion of a patient on the pressure sensing pad. Each pressure sensing pads is connected to one wireless control box, and the wireless control box automatically determines a status of the pressure sensing pad based on the electrical signal and a status of the connection between the wireless control box and the pressure sensing pad. The wireless control box generates a pressure-sensing signal that includes information relating to the status of the pressure sensing pad and connection between the wireless control box and the pressure sensing pad and then transmits the pressure-sensing signal via wireless transmission to a nurses station server. To transmit the pressure-sensing signal when the wireless control box and nurses station server are distant, a wireless router may be configured to receive the pressure-sensing signal sent from the wireless control box, and then forward the pressure-sensing signal to the nurses station server. The said pressure-sensing signal may also be forwarded to a cloud server and/or other central server. The system terminal equipment is connected with the nurses station server and is configured to receive the pressure-sensing signal from the nurses station server. The system terminal equipment may also be connected to a cloud server via a computer network, such as the internet, to transfer data in the pressure-sensing signal for remote storage. The nurses station server uses an algorithm to analyze the pressure-sensing signal and determine a patient's status and notify the on-duty personnel as configured in the nurses station. The mobile devices may be configured to receive the pressure-sensing signal from the system terminal equipment or the nurses station server, issue notifications to health care professionals, and/or retrieve stored data.

In view of the foregoing, the technical solutions of the present disclosure result in significant advantages and beneficial effects, when compared to existing techniques. The implementation of the above-mentioned technical solutions achieves substantial technical improvement and provides utility that is widely applicable in the health care industry. Specifically, technical advantages generally attained, by embodiments of the present invention, include:

(1) Updating the physiological information of the patients real-time;
(2) Providing a visual management interface that allows the nurses to quickly comprehend the patients' statuses;
(3) Providing a warning reminder so that health care professionals may provide timely assistance to patients;
(4) Storing historical data that assists doctors and nurses in providing effective health care;
(5) Enabling long-distance health care and improving the safety and quality of health care;
(6) Performing data analysis capable of timely determining patients' clinical conditions and notifying health care professionals of such conditions.

Many of the attendant features will be more readily appreciated and better understood with reference to the following detailed description considered in connection with the accompanying drawings.

BRIEF DESCRIPTION OF THE DRAWINGS

The present description will be better understood from the following detailed description read in light of the accompanying drawing, wherein.

DETAILED DESCRIPTION

Figure 1:
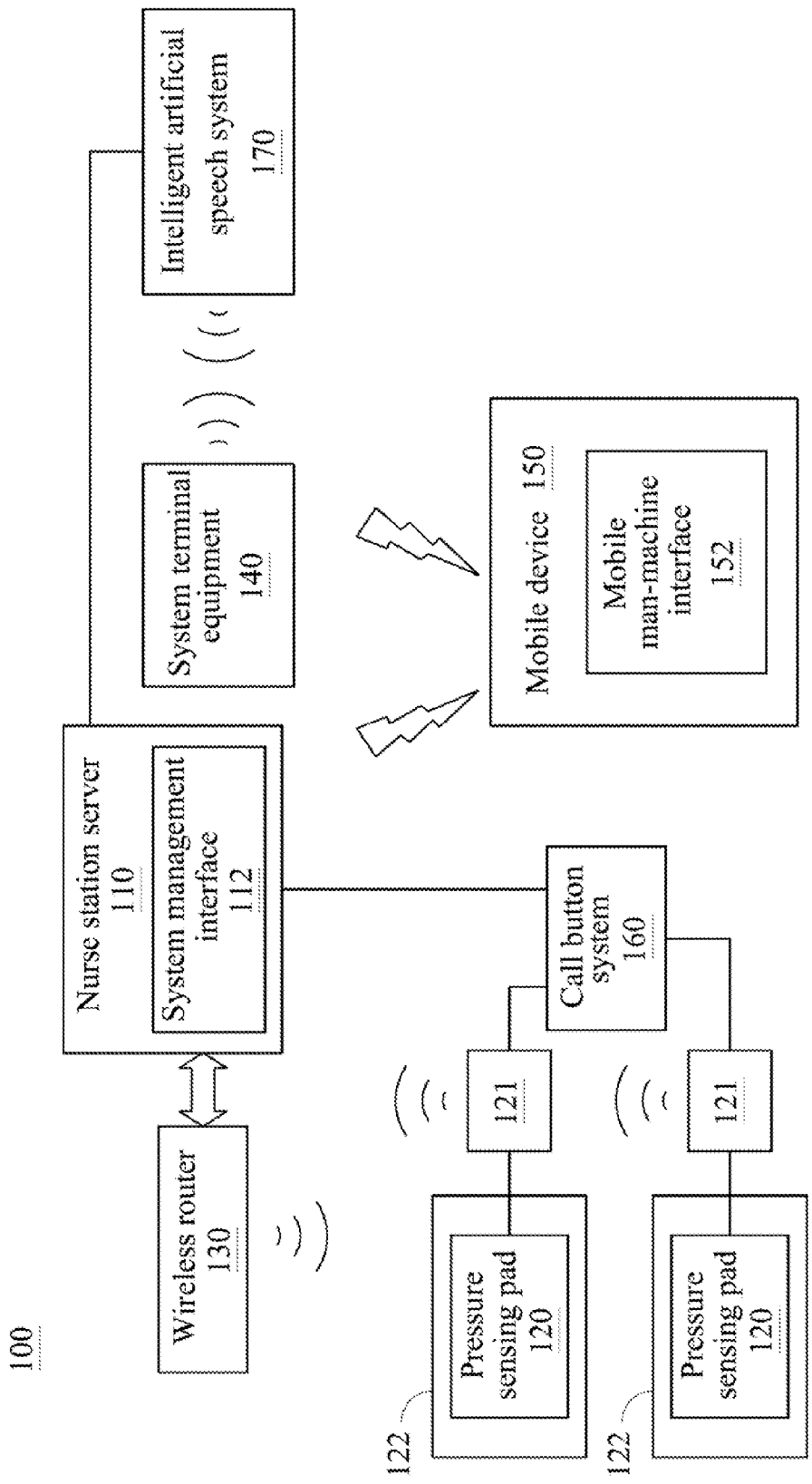
FIG. 1 is a block diagram illustrating a clinical information management system according to one embodiment of the present disclosure.

In the following detailed description, for purposes of explanation, numerous specific details are set forth in order to attain a thorough understanding of the disclosed embodiments. In accordance with common practice, the various described features/elements are not drawn to scale but instead are drawn to best illustrate specific features/elements relevant to the present invention. Also, like referenced numerals and designations in the various drawings are used to indicate like elements/parts. Moreover, well-known structures and devices are schematically shown in order to simplify the drawing and to avoid unnecessary limitation to the claimed invention.

With reference to FIG. 1, which is a block diagram illustrating a clinical information management system 100 according to one embodiment of the present disclosure, the clinical information management system 100 comprises a nurses station server 110, a plurality of pressure sensing pads 120, a plurality of wireless control boxes 121, a wireless router 130, system terminal equipment 140, and a mobile device 150.

The plurality of pressure sensing pads 120 are distributed to a plurality of beds 122, wherein each of the pressure sensing pads is connected with one wireless control box 121 (including a Bluetooth transceiver and/or a Wi-Fi transceiver); and when the pressure sensing pads and the wireless control box are connected, the wireless control box determines the size or type of the pressure sensing pad. In practice, the wireless control box 121 can be situated inside or outside the pressure sensing pads 120, and persons having ordinary skill in the art can select at their option the desired arrangement depending on actual need. Each of the pressure sensing pads 120 is configured to generate an electrical signal in response to the presence and motion of a patient on the pressure sensing pad. Each of the pressure sensing pads 120 is connected to one wireless control box 121, and the wireless control box 121 automatically determines a status of the pressure sensing pad 120 based on the electrical signal and a status of the connection between the wireless control box 121 and the pressure sensing pad 120. The wireless control box 121 generates a pressure-sensing signal that includes information relating to the said status of the pressure sensing pad and connection between the wireless control box and the pressure sensing pad and then transmits the pressure-sensing signal via wireless transmission to a nurses station server 110. The nurses station server 110 computes from the pressure-sensing signal a pressure distribution status, which describes the position of the patient on the pressure sensing pad 120. To transmit the pressure-sensing signal when the wireless control box 121 and nurses station server 110 are distant, a wireless router 130 may be configured to receive the pressure-sensing signal sent from the wireless control box 121, and then forward the pressure-sensing signal to the nurses station server 110. The said pressure-sensing signal may also be forwarded to a cloud server or other central server. The system terminal equipment 140 is connected with the nurses station server 110, and is configured to receive the pressure-sensing signal from the nurses station server 110. The mobile device 150 is configured to receive the pressure-sensing signal from the system terminal equipment 140 or the nurses station server 110.

In one embodiment, the system terminal equipment 110 can be a hospital information system or a cloud server, which is connected with the nurses station server 110 via the internet, so as to record the physiological information of a patient based on the pressure-sensing signal.

In one embodiment, the mobile device 150 is a medical rounds cart, hand-held mobile device, or wearable device, so as to facilitate the work of nurses.

In one embodiment, the nurses station server 110 is configured to present a system management interface 112 based on the pressure-sensing signal, and the system management interface 112 displays a visual representation of the pressure distribution status of a plurality of pressure sensing pads 120. In practice, when the system management interface 112 remains idle for an extended period of time (e.g., more than 10 minutes), it will automatically lock and the nurse must re-authenticate with an account identifier and password, so as to improve information security.

In one embodiment, the nurses station server 110 or the system terminal equipment 140 calculates an activity status curve of a patient on the bed 122 illustrating how the pressure distribution status has changed over a period of time, and the nurses station server 110 uses the system management interface to display the activity status curve.

In one embodiment, the nurses station server 110 or system terminal equipment 140 calculates the body posture and relative position of a patient on the bed 122 using the pressure distribution status, and the nurses station server uses the system management interface 112 to display a visual representation of the body posture and relative position.

In one embodiment, when the pressure distribution status of one pressure sensing pad of the pressure sensing pads 120 changes after the pressure distribution status remains constant for a pre-determined time and the change of the pressure distribution status satisfies a set of threshold criteria, the wireless control box 121 transmits an awakening notification as part of the pressure-sensing signal to the nurses station server 110. Correspondingly, the nurses station server 110 uses the system management interface 112 to display an awakening notification corresponding to the one pressure sensing pad, so as to alert the nurses that the patient may be awake. In practice, the set of threshold criteria can be flexibly adjusted by a system designer.

In one embodiment, a path of patient movement is computed from changes in the pressure distribution status based on patient movement over a period of time on one pressure sensing pad of the pressure sensing pads 120. When the path of patient movement indicates the patient moves from the center towards the periphery or corner of the one pressure sensing pad, the patient sits up on the corresponding bed 122, or the lower part of the patient's body moves towards the periphery of the bed 122, the wireless control box 121 triggers an alarm (e.g., a sound signal, a light signal, etc.) by the bed 122; correspondingly, the wireless control box 121 transmits a leaving-bed warning message as part of the pressure-sensing signal to the nurses station server 110. The nurses station server 110 uses the system management interface 112 to display a leaving-bed warning message corresponding to the one pressure sensing pad.

In one embodiment, a path of patient movement is computed from changes in the pressure distribution status based on patient movement over a period of time on one pressure sensing pad of the pressure sensing pads 120. When the path of patient movement indicates the patient from the center towards the periphery or corner of the one pressure sensing pad, the wireless control box 121 triggers an alarm by the bed 122; correspondingly, the wireless control box 121 transmits a falling-off-bed attention message as part of the pressure-sensing signal to the nurses station server 110. The nurses station server 110 uses the system management interface 112 to display a falling-off-bed attention message corresponding to the one pressure sensing pad, so as to alert the nurses to check on the patient.

In one embodiment, when one pressure sensing pad of the pressure sensing pads 120 cannot detect any pressure for a period of time configured in the wireless control box 121 or nurses station server 110, it suggests that a patient has left the bed, and the wireless control box 121 transmits a left-the-bed notification as part of the pressure-sensing signal to the nurses station server 110. The nurses station server 110 uses the system management interface 112 to display a left-the-bed notification corresponding to the one pressure sensing pad, so as to alert the nurses to determine the whereabouts of the patient, and the nurses station server 110 tracks the left-the-bed time until the patient returns to the bed and is repositioned on the pressure sensing pad 120.

In one embodiment, when the pressure of a portion of one pressure sensing pad of the pressure sensing pads 120 (e.g., the portion of one pressure sensing pad under the patient's legs, chest, etc.) does not change after a preset time, it means that the patient may need to be repositioned to reduce the risk of pressure ulcers. Hence, the wireless control box 121 triggers an alarm by the bed 122 and transmits a patient repositioning reminder message as part of the pressure-sensing signal to the nurses station server 110; correspondingly, the nurses station server 110 uses the system management interface 112 to display a patient repositioning reminder message corresponding to the one pressure sensing pad, so as to remind the nurses to reposition the patient. In practice, the specific value of the "preset time" can be flexibly adjusted by a system designer; for example, the preset time can be set at 2 hours.

In one embodiment, when the pressure distribution status corresponding to one pressure sensing pad 120 indicates that pressure, as measured by the pressure sensing pad 120, exerted by the patient over 80% to 100% of the surface area of the pressure sensing pad 120 has not changed over a preset time interval, there exists immobilization of the patient that may indicate a negative patient health condition. The wireless control box 121 triggers an alarm by the bed 122; correspondingly, the wireless control box transmits an immobilization message as part of the pressure-sensing signal to the nurses station server 110. The nurses station server 110 uses the system management interface 112 to display an immobilization notification corresponding to the one pressure sensing pad, so as to alert the nurses to check the patient's vital signs.

In one embodiment, when a battery level of one wireless control box of the wireless control boxes 121 is lower than a pre-determined battery level, the wireless control box 121 triggers an alarm by the bed 122; correspondingly, the wireless control box transmits a low-battery message as part of the pressure-sensing signal to the nurses station server 110. The nurses station server 110 uses the system management interface 112 to display a low-battery message corresponding to the one wireless control box, so as to notify the nurse to change the battery.

In one embodiment, when the nurses station server 110 does not receive the pressure-sensing signal of the wireless control box 121 of one pressure sensing pad of the pressure sensing pads 120, thereby resulting in the nurses station server 110's failure to monitor the physiological information of the patient in the bed 122 corresponding to the wireless control box 121 in real-time, the nurses station server 110 uses the system management interface 112 to display a signal-interrupted message corresponding to the one pressure sensing pad, so as to notify relevant personnel to perform an inspection.

In one embodiment, when the nurses station server 110, during a period of time, detects delays in the arrival of the pressure-sensing signal of the wireless control box 121 of one pressure sensing pad of the pressure sensing pads 120, and the number of instances of delay achieves a preset number, the nurses station server 110 uses the system management interface 112 to display a low-transmission-quality message corresponding to the one pressure sensing pad.

In one embodiment, when the nurses station server 110, during a period of time, detects delays in the arrival of the pressure-sensing signal of the wireless control box 121 of one pressure sensing pad of the pressure sensing pads 120, and the number of instances of delay achieves a preset number, the nurses station server 110 sends a low-transmission-quality message to the mobile device 150 and/or to the system terminal equipment 140 which further to send a low-transmission-quality message to the mobile device 150. The mobile device 150 uses a mobile user interface 152 to display a low-transmission-quality message corresponding to the one pressure sensing pad.

In one embodiment, when the variation of the pressure-sensing signal of one pressure sensing pad of the pressure sensing pads 120 is maintained at a preset value and for a pre-determined amount of time, the nurses station server uses the system management interface 112 to display a patient-convulsion notification.

In one embodiment, when the pressure-sensing signal of one pressure sensing pad of the pressure sensing pads 120 is used to determine the patient body weight, and when the body weight varies above an upper-limit value or below a lower-limit value, the nurses station server 110 uses the system management interface 112 to display a patient-body-weight-variation notification.

In one embodiment, when the pressure-sensing signal of one pressure sensing pad of the pressure sensing pads 120 generates a variation at a fixed frequency, the nurses station server 110 is configured to detect a patient's respiration rate or heart rate, and when the patient's respiration rate or heart rate is above an upper-limit value or when the patient's respiration rate or heart rate is below a lower-limit value, the nurses station server 110 uses the system management interface 112 and/or the mobile device 150 uses the mobile user interface 152 to transmit a patient-breath-or-heartbeat-abnormal notification.

In one embodiment, a healthcare professional uses a system management interface 112 of the nurses station server 110 or a mobile user interface 152 of the mobile device 150 to input or update a patient-fall-risk assessment and a bedsore-risk assessment. The nurses station server 110 monitors a bedridden patient's activity status in real-time and connects with the hospital information system to obtain a patient-medication status; and a system management interface 112 or a mobile user interface 152 displays an updated patient-fall-risk index and bedsore-risk index that is derived from the bedridden patient's activity status and the patient-medication status.

In one embodiment, when the wireless control box 121 detects that one pressure sensing pad of the pressure sensing pads 120 is removed or has a loose contact, the wireless control box 121, for example, triggers an alarm by the bedside and/or transmits a pressure-sensing-pad-removed-or-loose-contact message to the nurses station server 110; correspondingly, the nurses station server 110 uses the system management interface 112 to display a pressure-sensing-pad-removed or inadequate-contact signal corresponding to the one pressure sensing pad.

In one embodiment, when the pressure sensing pads 120 and the wireless control box 121 are connected, the wireless control box 121 determines the size or type of the pressure sensing pads 120, and the nurses station server 110 uses the system management interface 112 to display the size and type corresponding to the pressure sensing pads 120.

The mobile device 150 is configured to modify the information displayed on a mobile user interface 152 based on the pressure-sensing signal, and the mobile user interface 152 displays a pressure distribution status of any one of a plurality of pressure sensing pads 120. In practice, when the mobile user interface 152 remains inactive for an extended period of time (e.g., exceeding 10 minutes) it will automatically lock and the nurse must re-authenticate with an account identifier and password, so as to ensure information security. A mobile application software (e.g., APP) can be installed in the mobile device to display the mobile user interface 152.

In one embodiment, when the pressure distribution status of one pressure sensing pad of the pressure sensing pads 120 changes after the pressure distribution status remains constant for a pre-determined time and the change in the pressure distribution status satisfies a threshold criteria, the mobile device 150 uses the mobile user interface 152 to transmit an awakening notification corresponding to the one pressure sensing pad, so as to alert the nurses that the patient may be awake.

In one embodiment, when a path of patient movement computed from changes in the pressure distribution status based on patient movement over a period of time on one pressure sensing pad of the pressure sensing pads 120 indicates the patient moves from the center towards the periphery or corner of the one pressure sensing pad, suggesting that a patient may fall off the bed, the mobile device 150 uses the mobile user interface 152 to display a falling-off-bed attention message corresponding to the one pressure sensing pad, so as to alert the nurses to check on the patient.

When a path of patient movement computed from changes in the pressure distribution status based on patient movement over a period of time on one pressure sensing pad of the pressure sensing pads 120 indicates the patient moves from the center towards the periphery or corner of the one pressure sensing pad, the patient sits up from the corresponding bed 122, or the lower part of the patient's body moves towards the periphery of the bed 122, the mobile device 150 uses the mobile user interface 152 to display a leaving-bed warning message corresponding to the one pressure sensing pad.

In one embodiment, when one pressure sensing pad of the pressure sensing pads 120 cannot detect any pressure for a period of time configured in the wireless control box 121 or nurses station server 110, it suggests that a patient has left the bed, and the mobile device 150 uses the mobile user interface 152 to display a left-bed notification corresponding to the one pressure sensing pad, so as to alert the nurses to determine the whereabouts of the patient.

In one embodiment, when the pressure on a portion of one pressure sensing pad of the pressure sensing pads 120 (e.g., the portion of one pressure sensing pad under the patient's leg, chest, etc.) does not change after a preset time, it means that the patient may need to be repositioned to reduce the risk of pressure ulcers, and the mobile device 150 uses the mobile user interface 152 to transmit a patient repositioning reminder message corresponding to the one pressure sensing pad, so as to remind the nurses to reposition the patient.

In one embodiment, when the pressure distribution status corresponding to one pressure sensing pad 120 indicates that pressure, as measured by the pressure sensing pad 120, exerted by the patient over 80% to 100% of the surface area of the pressure sensing pad 120 has not changed over a preset time interval, there exists immobilization of the patient that may indicate a negative patient health condition. The mobile device 150 uses the mobile user interface 152 to transmit an immobilization notification corresponding to the one pressure sensing pad, so as to alert the nurses to check the patient's vital signs.

In one embodiment, when a battery level of one wireless control box of the wireless control boxes 121 is lower than a pre-determined battery level, the mobile device 150 uses the mobile user interface 152 to transmit a low-battery message corresponding to the one wireless control box, so as to notify the nurse to change the battery.

In one embodiment, when the nurses station server 110 does not receive the pressure-sensing signal of the wireless control box 121 of one pressure sensing pad of the pressure sensing pads 120, thereby resulting in the nurses station server 110's failure to monitor the physiological information of the patient in real-time, the mobile device 150 uses the mobile user interface 152 to transmit a signal-interrupted message corresponding to the one pressure sensing pad, so as to notify relevant personnel to perform an inspection.

In one embodiment, when the wireless control box 121 detects that one pressure sensing pad of the pressure sensing pads 120 is removed or has a loose contact, the wireless control box 121 transmits a pressure-sensing-pad-removed-or-loose-contact message to the nurses station server 110, and the mobile device 150 uses the mobile user interface 152 to transmit a pressure-sensing-pad-removed or inadequate-contact message corresponding to the one pressure sensing pad 120.

In one embodiment, clinical information management system 100 comprises a call button system 160. In structure, the call button system 160 is connected with the wireless control box 121. In use, if the patient activates the call button system 160, or if it is detected that the patient leaves the bed via the above-described mechanism, the wireless control box 121 triggers an alarm signal, and the nurses station server 110 transmits the alarm signal, via for example a wireless transceiver or wired LAN connection, to establish a text or voice communication with the mobile device 150, so that the relevant personnel are apprised of the event associated with the alarm and can handle the situation.

Moreover, when the wireless control box 121 triggers the alarm signal, the healthcare professional can have a conversation with the patient via the system management interface 112 of the nurses station server 110 or the mobile user interface 152 of the mobile device 150. In practice, the wireless control box 121 has a built-in or external microphone for implementing the voice communication.

In one embodiment, clinical information management system 100 comprises an intelligent artificial speech system 170. In structure, the intelligent artificial speech system 170 may employ a wired or wireless connection to the system terminal equipment 140 or the nurses station server 110. In use, when the system terminal equipment 140 or the nurses station server 110 detects an alarm signal, the intelligent artificial speech system 170 can, in real-time, transmit a voice file to the wireless control box 121, and then have a conversation with the patient via the wireless control box 121. In practice, the wireless control box 121 can have a built-in or external microphone to enable voice communication.

When the nurses station server 110 stores the data in the system terminal equipment 140, the data is encrypted, and a data transmission verification is performed so as to ensure information security.

In practice, the clinical information management system 100 can be applied in hospitals, long-term care facilities or patients' homes, and persons having ordinary skill in the art may choose at their option among the available applications depending on actual need.

Figure 2:
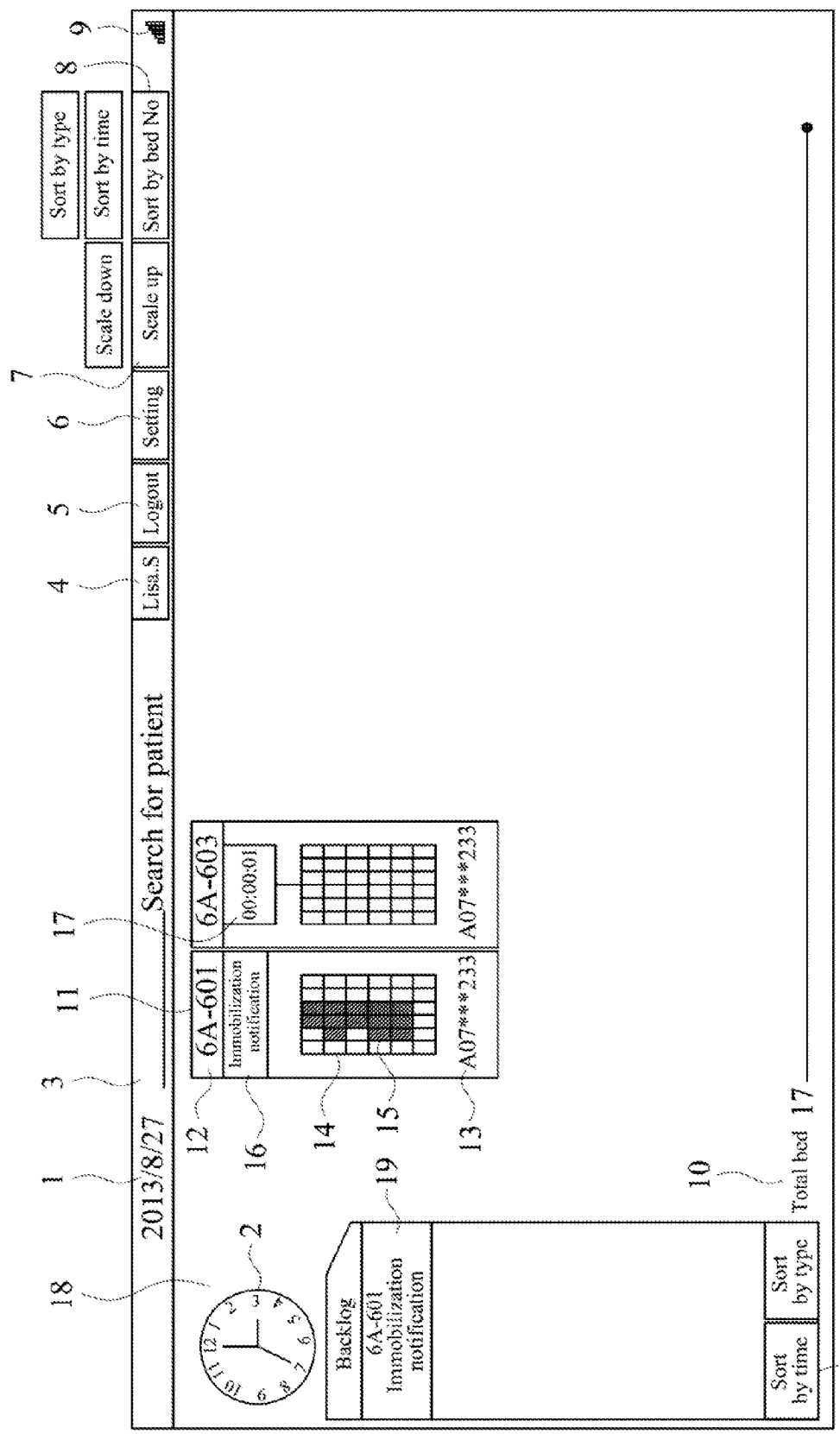
FIG. 2 is a schematic diagram illustrating a system management interface according to one embodiment of the present disclosure.

To provide a more specific description regarding the above-mentioned system management interface 112, refer to FIG. 2 which is a schematic diagram illustrating a system management interface 112 according to one embodiment of the present disclosure. As illustrated in FIG. 2, the screen displayed by the system management interface 112 includes date 1, time 2, pressure sensing pad search field 3, user account 4, "user logout" option 5, system settings 6, pressure sensing pad image scaling 7, "pressure sensing pad sorting/selection" option 8, network signal strength 9, total number 10 of connected pressure sensing pads, display 11 of all connected pressure sensing pads, pressure sensing pad number 12, medical history number 13, pressure sensing pad matrix 14, pressure distribution status 15, wireless control box alarm information 16, tracking time of leaving-bed events 17, overview of pressure sensing pads covering the above-mentioned information 18, list of backlog messages 19, and event sorting/selection option 20. In practice, a nurse may consider that pressure sensing pads represented on the system management interface 112 correspond to beds occupied by patients receiving care.

The overview of pressure sensing pad 18 provides the nurses visual information about the pressure sensing pads 120, comprising: the size of the pressure sensing pads 120, the variation of pressure points, and various alarm information displayed in different colors. The list of backlog messages 19 arranges and presents the information relevant to nurses in a list.

In FIG. 2, the pressure sensing pad alarm information 16 is an immobilization notification message; however the present disclosure is not limited thereto; in practice, the pressure sensing pad alarm information 16 can display information reflecting a variety of actual conditions, e.g., the above-mentioned awakening notification, falling-off-bed attention message, leaving-bed warning message, pressure-reduction reminder message, left-bed notification, immobilization notification, low-battery message, signal-interrupted message, pressure-sensing-pad-removed or inadequate-contact message or other information.

Figure 3:
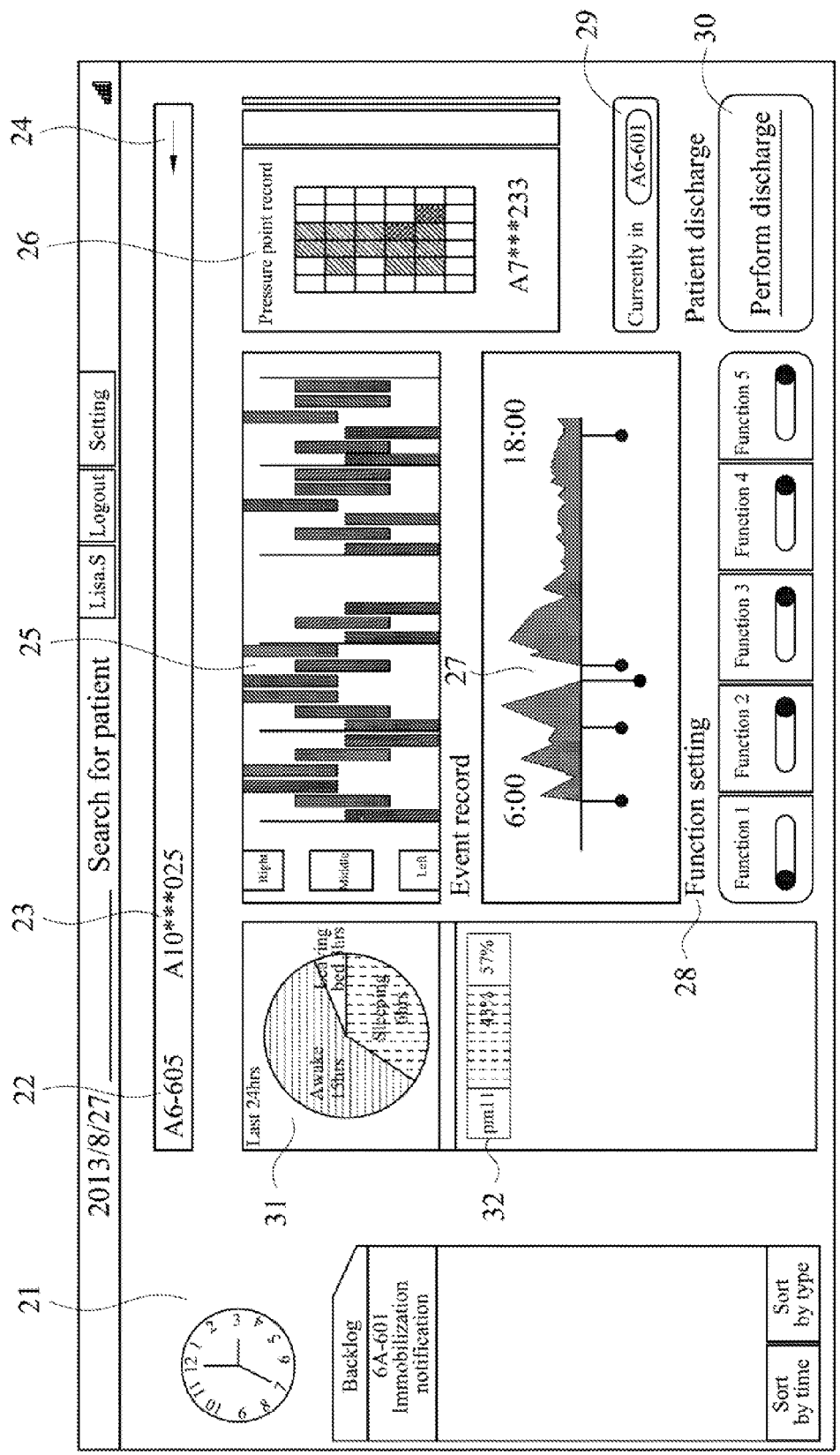
FIG. 3 is a schematic diagram illustrating a system management interface according to another embodiment of the present disclosure.

FIG. 3 is a schematic diagram illustrating a system management interface according to another embodiment of the present disclosure. As illustrated in FIG. 3, the system management interface can display screens associated with the status of any one of the pressure sensing pads; the said screen includes the historical data and setting of the pressure sensing pad 21, pressure sensing pad number 22, medical history number 23, "return to previous page" option 24, pie chart of daily activity record 31, bar graph of hourly activity record and ratio thereof 32, distribution diagram of patient position record 25, distribution diagram of pressure point record 26, event record 27, function settings menu 28, "bed adjustment settings" option 29 and "patient discharge setting" option 30.

It should be noted that the function settings menu 28 can be modified by the nurses to display pressure sensing pad alarm information as needed depending on the actual conditions of the patient.

Figure 4:
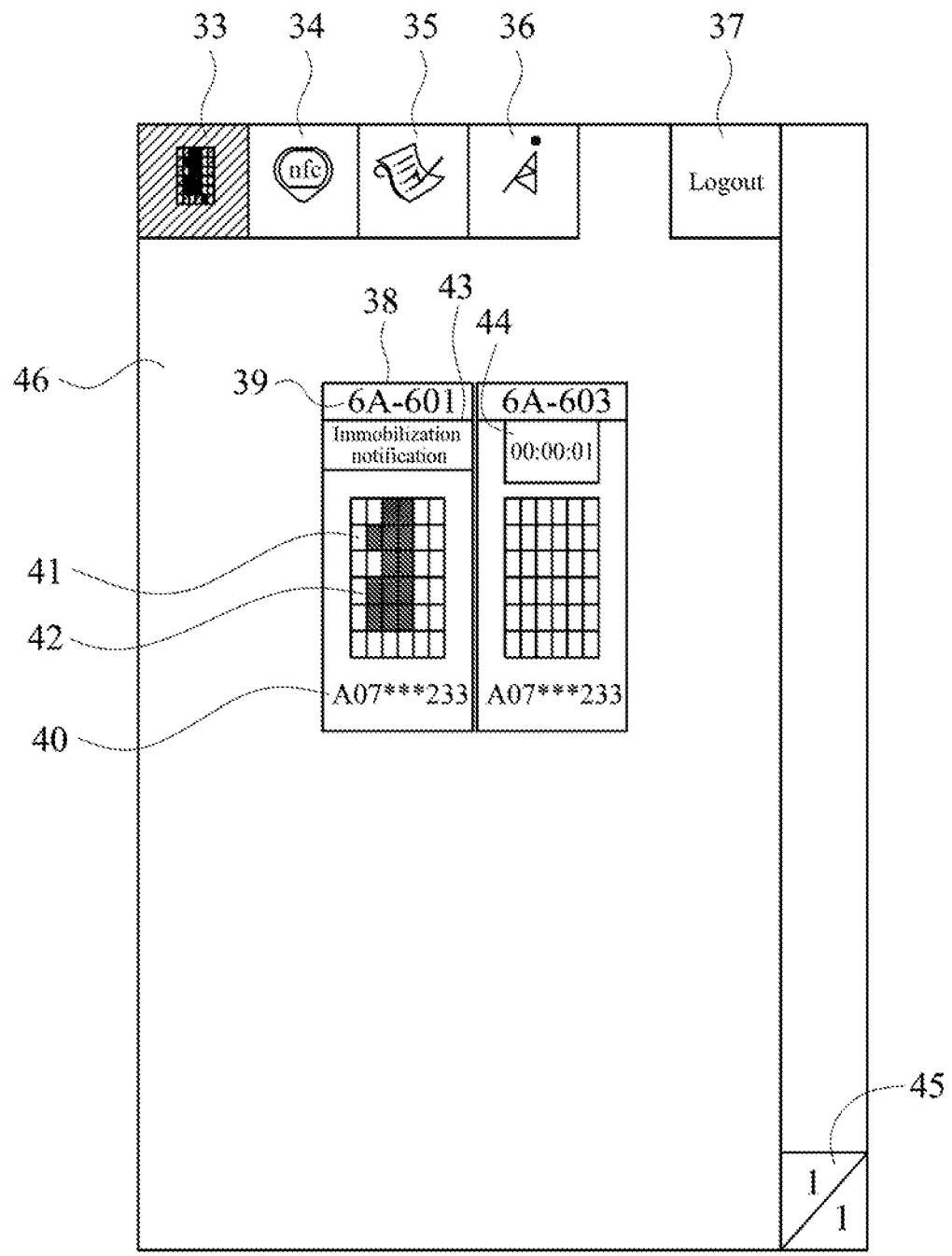
FIG. 4 is a schematic diagram illustrating a mobile user interface according to one embodiment of the present disclosure.
Figure 5:
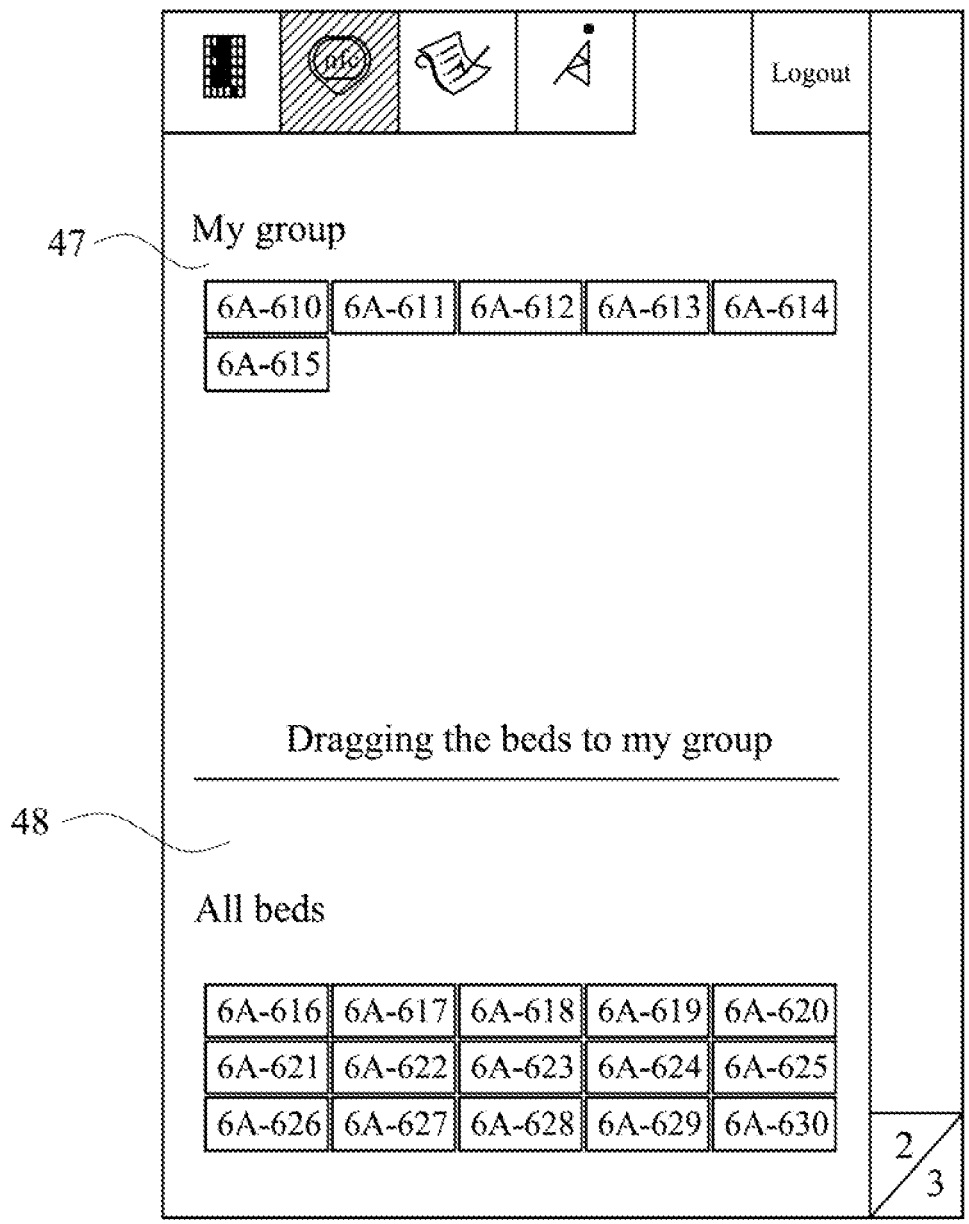
FIG. 5 is a schematic diagram illustrating a mobile user interface according to another embodiment of the present disclosure.

To provide a more specific description regarding the above-mentioned mobile user interface, the attention is brought to FIGS. 4 and 5, which schematically illustrate a mobile user interface according to one embodiment of the present disclosure. As illustrated in FIG. 4, the screen displayed by the mobile user interface includes, "overview of pressure sensing pads" option 33, "pressure sensing pads settings" option 34, "overview of backlog messages" option 35, "connection settings" option 36, "user logout" option 37, page number and total number of pages 45, overview 46 of connected pressure sensing pads, display 38 of all connected pressure sensing pads, pressure sensing pad number 39, medical history number 40, pressure sensing pad matrix 41, pressure distribution status 42, pressure sensing pad alarm information 43, tracking time of leaving-bed events 44, group of pressure sensing pads managed by the user 47 and list 48 of all pressure sensing pads.

It should be noted that group of pressure sensing pads managed by the user 47 allows the mobile device used by a particular nurse to display the information of pressure sensing pads upon which the nurse must focus.

In FIG. 4, the pressure sensing pad alarm information 43 is an immobilization notification; however the present disclosure is not limited thereto; in practice, pressure sensing pad alarm information 43 can display information reflecting a variety of actual conditions, e.g., the above-mentioned awakening notification, falling-off-bed attention message, leaving-bed warning message, pressure-reduction reminder message, left-bed notification, immobilization notification, low-battery message, signal-interrupted message, pressure-sensing-pad-removed or inadequate-contact message or other information.

Figure 6:
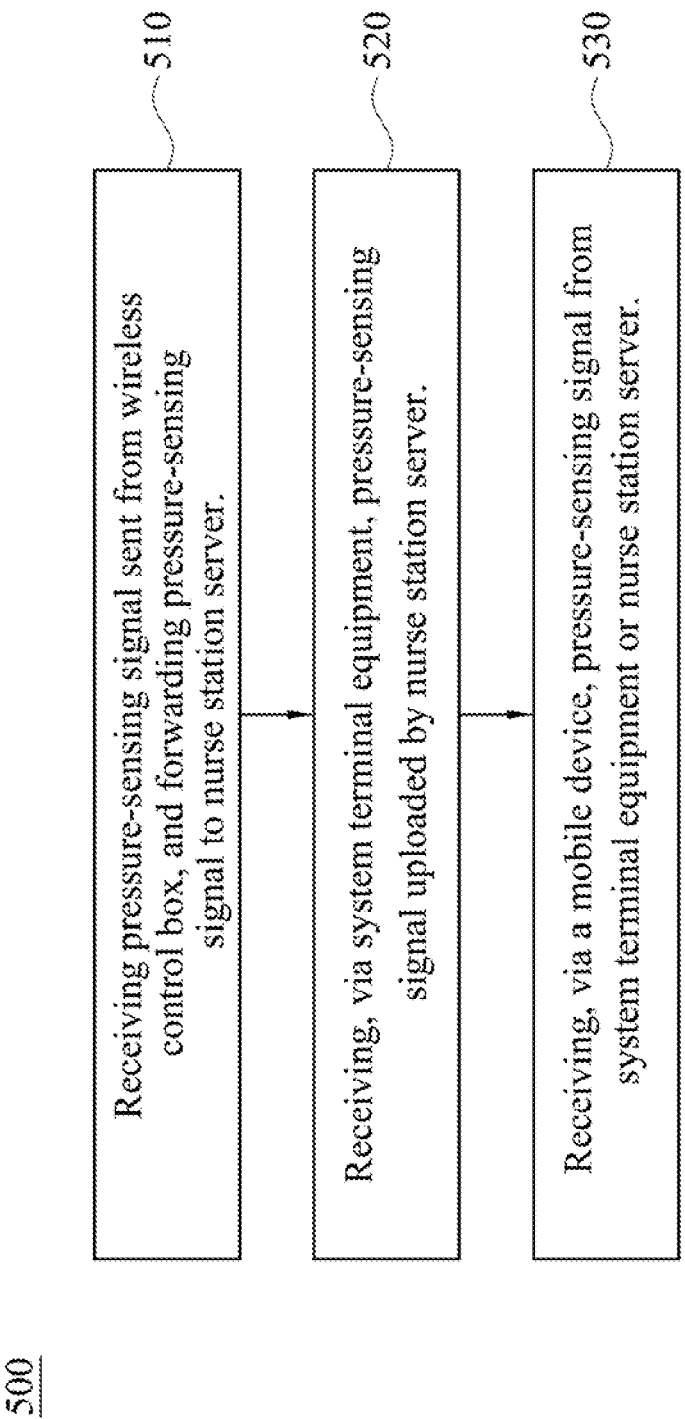
FIG. 6 is a flow chart illustrating a method for managing hospital beds according to one embodiment of the present disclosure.

FIG. 6 is a flow chart illustrating a method 500 for managing hospital beds according to one embodiment of the present disclosure. As illustrated, the method 500 for managing hospital beds comprises steps 510 to 530. It should be appreciated that the steps recited in the present embodiments are exemplary. The sequence of the steps may be interchangeable, and all or part of the steps may be simultaneously, partially simultaneously, or sequentially performed.

In the method 500 for managing hospital beds, a plurality of pressure sensing pads are distributed to a plurality of beds, and each of the pressure sensing pads is connected with a wireless control box; in step 510, a pressure-sensing signal sent from the wireless control box is received by a nurses station server; in step 520, the pressure-sensing signal received by the nurses station server is transmitted to a system terminal equipment; in step 530, the pressure-sensing signal received by the system terminal equipment or the nurses station server is transmitted to a mobile device.

In the method 500 for managing hospital beds, the mobile device modifies the display of a mobile user interface based on the pressure-sensing signal, and the mobile user interface displays the pressure distribution status of any one of the plurality of pressure sensing pads. Moreover, the mobile user interface also, depending on the actual conditions of the pressure sensing pads, displays a pressure-reduction reminder message, awakening notification, falling-off-bed attention message, leaving-bed warning message, pressure-reduction reminder message, left-bed notification, immobilization notification, low-battery message, signal-interrupted message, pressure-sensing-pad-removed or inadequate-contact, or other communications about patient status determined from the pressure-sensing signal or any other information; as to the specific mechanisms or conditions for displaying or transmitting the message or notification, since they are described in the above-mentioned embodiments, they are not repeated herein for the sake of brevity.

On the other hand, in the method 500 for managing hospital beds, the nurses station server is configured to display a system management interface based on the pressure-sensing signal, and the system management interface displays the pressure distribution status of the plurality of pressure sensing pads. Similarly, the system management interface can, depending on the actual condition, transmit a pressure-reduction reminder message, awakening notification, falling-off-bed attention message, leaving-bed warning message, pressure-reduction reminder message, left-bed notification, immobilization notification, low-battery message, signal-interrupted message, pressure-sensing-pad-removed or inadequate-contact message, or other communications about patient status determined from the pressure-sensing signal or any other information.

Figure 7A:
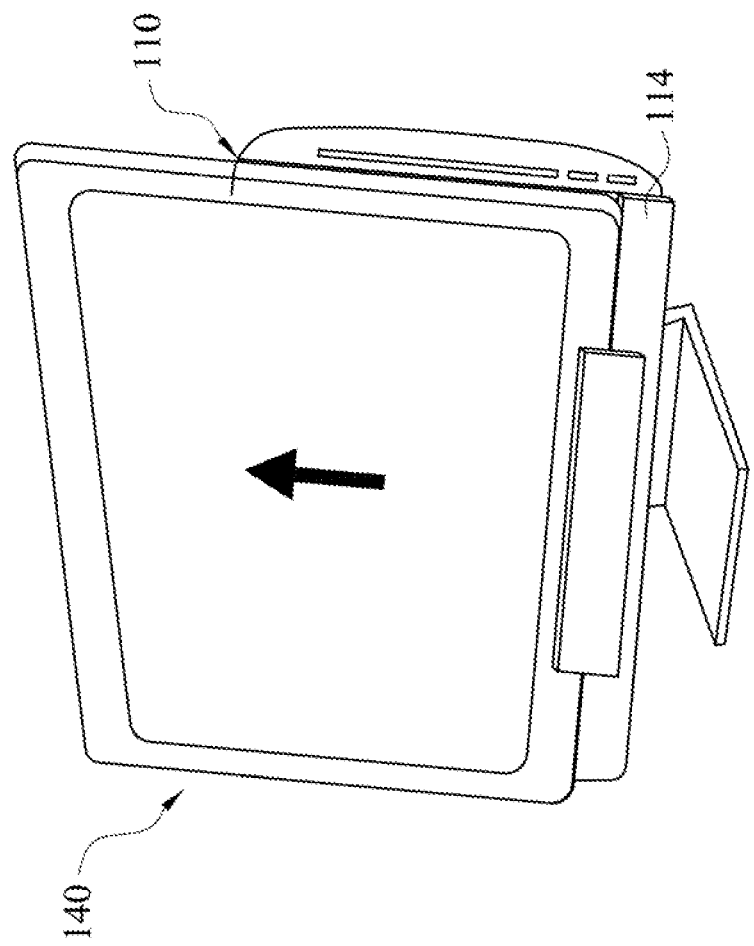
FIG. 7A is a perspective view illustrating system terminal equipment combined with a nurses station server according to one embodiment of the present disclosure.
Figure 7B:
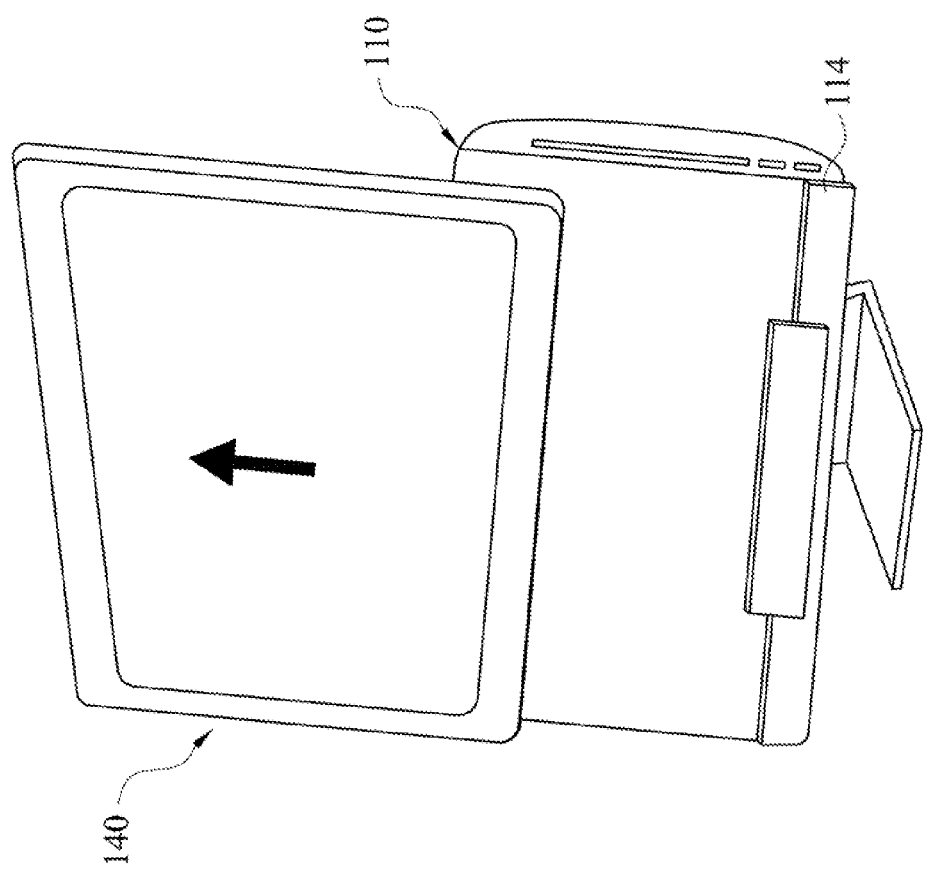
FIG. 7B is a perspective view illustrating system terminal equipment separated from a nurses station server according to one embodiment of the present disclosure.

FIG. 7A is a perspective view illustrating a system terminal equipment combined with a nurses station server 110 according to one embodiment of the present disclosure; FIG. 7B is a perspective view illustrating a system terminal equipment 140 separated from a nurses station server 110 according to one embodiment of the present disclosure. As illustrated in FIGS. 7A and 7B, the system terminal equipment 140 is connected to the dual system base 114. When the nurses station server 110 is connected to the dual system base 114, the display of the nurses station server 110 can serve as the display device for the system terminal equipment 140. When the nurses station server is separated from the dual system base 114, the nurses station server 110 and the system terminal equipment 140 function as independent devices. For example, the nurses station server 110 can be a tablet running an Android operating system, and the system terminal equipment 140 can be a computer running a Microsoft Windows operating system (e.g., Windows 8).

Figure 8:
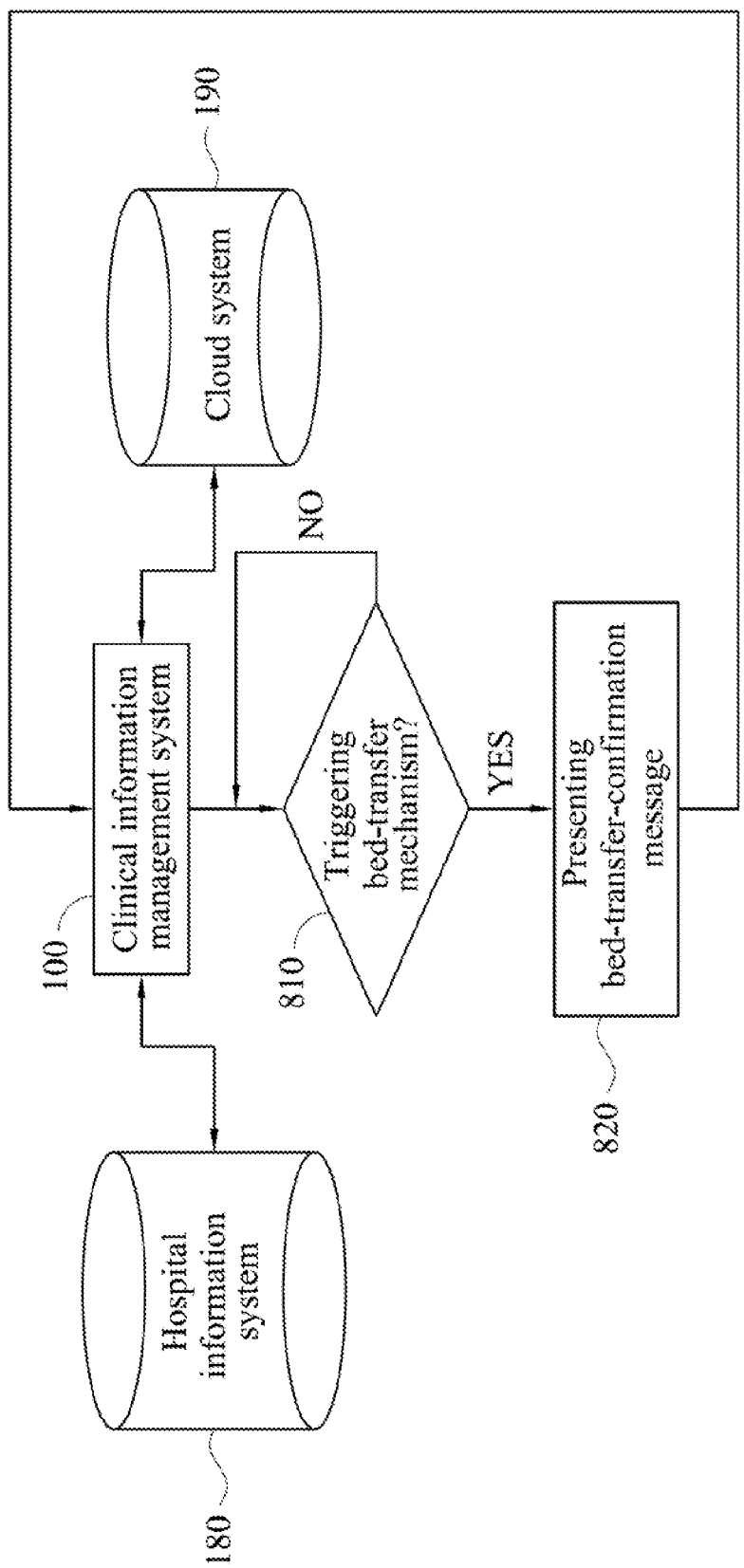
FIG. 8 is a flow chart illustrating the process of automatic detection of bed-transfer according to one embodiment of the present disclosure.

FIG. 8 is a flow chart illustrating the process of automatic detection of bed-transfer according to one embodiment of the present disclosure; as illustrated in FIG. 8, the clinical information management system 100 connects to a hospital information system 180 and a cloud system 190. In the present embodiment, the term "bed transfer" refers to the situation where a patient is transferred from one particular bed to another bed; referring to both FIGS. 1 and 8, in step 810, it is determined whether to trigger a bed-transfer mechanism, when the system terminal equipment 140 or the nurses station server 110 patient-bed-transfer notification is transmitted via the hospital information system 180, or when the system terminal equipment 140 or the nurses station server 110 automatically detects patient-repeated-admission information; in step 820, the nurses station server 110 uses the system management interface 112 to transmit a corresponding bed-transfer-confirmation message, and/or the mobile device 150 uses the mobile user interface to transmit a corresponding bed-transfer-confirmation message.

Figure 9:
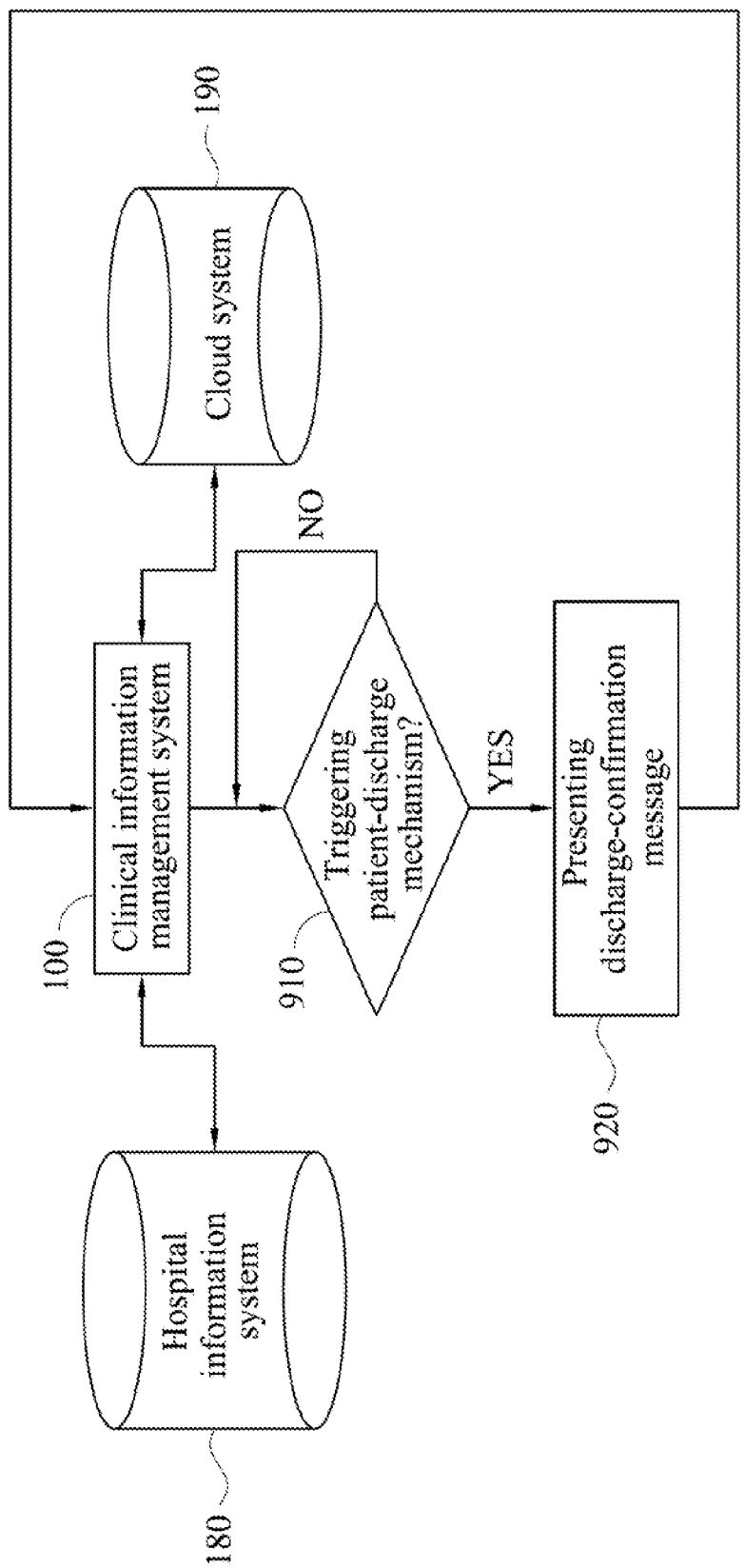
FIG. 9 is a flow chart illustrating the process of automatic detection of patient-discharge according to one embodiment of the present disclosure.

FIG. 9 is a flow chart illustrating the process of automatic detection of patient-discharge according to one embodiment of the present disclosure; as illustrated in FIG. 9, the clinical information management system 100 connects to a hospital information system 180 and a cloud system 190. In the present embodiment, the term "patient discharge" refers to the situation where the patient is discharge from the hospital or is transferred to a floor level or ward belonging to another nurses station; referring to both FIGS. 1 and 9, in step 910, it is determined whether to trigger a patient-discharge mechanism, when the system terminal equipment 140 or the nurses station server 110 obtains a patient-discharge information via the hospital information system 180, or after a patient leaves the corresponding bed for a pre-determined and the system terminal equipment 140 or the nurses station server 110 detects that the corresponding pressure sensing pad 120 is removed; in step 920, the nurses station server 110 uses the system management interface 112 to transmit a corresponding discharge-confirmation message, and/or the mobile device 150 uses the mobile user interface 152 to transmit a corresponding discharge-confirmation message.

Figure 10:
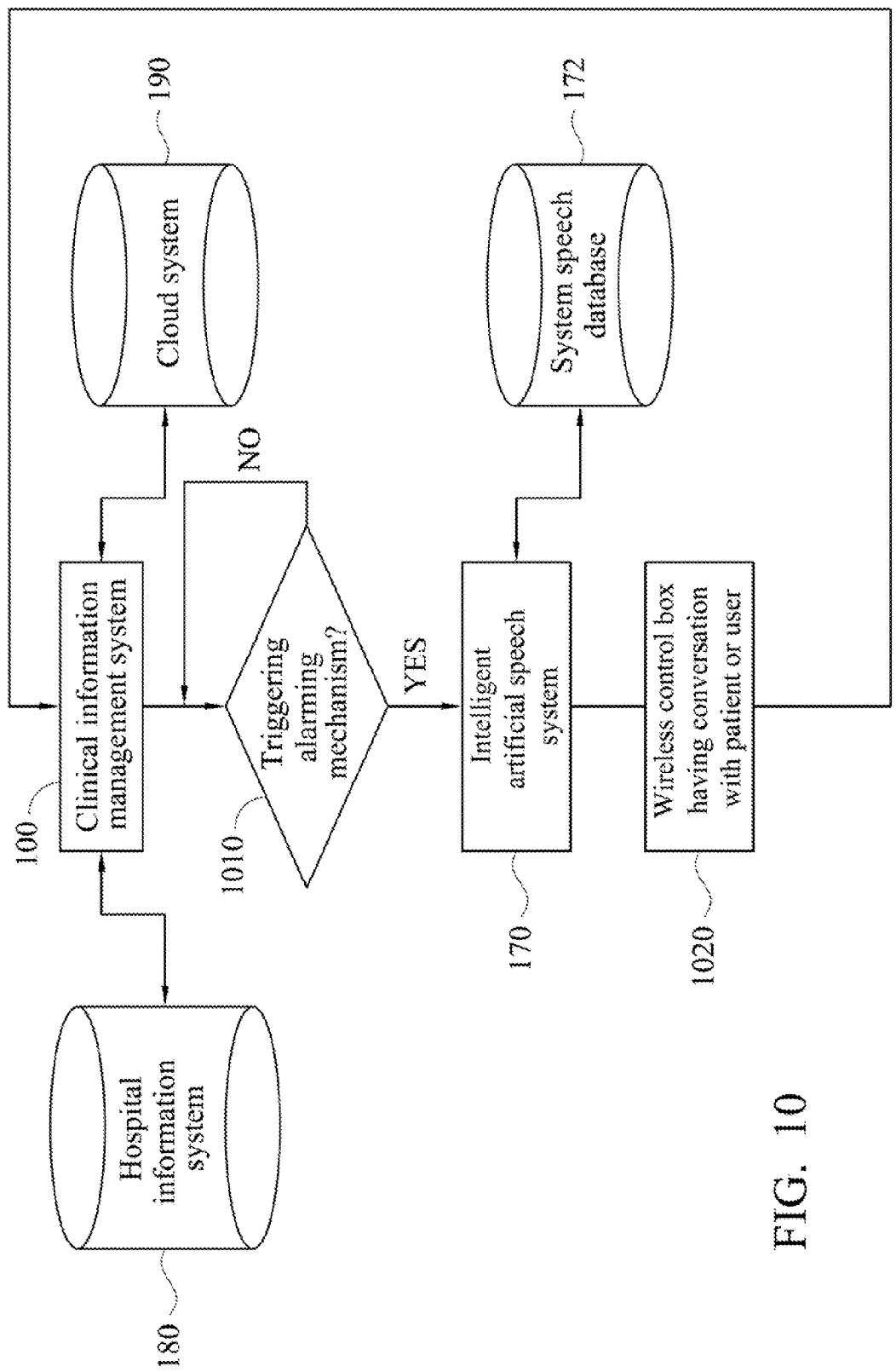
FIG. 10 is a flow chart illustrating the process of automatic artificial voice reminder according to one embodiment of the present disclosure.

FIG. 10 is a flow chart illustrating the process of automatic artificial voice reminder according to one embodiment of the present disclosure. As illustrated in FIG. 10, the clinical information management system 100 connects to a hospital information system 180 and a cloud system 190, and the intelligent artificial speech system 170 is connected with a system speech database 172. Referring to both FIGS. 1 and 10, in step 1010, it is determined whether to trigger an alarm mechanism (e.g., patient pressing the call button, patient leaving the bed, etc.). If a positive determination is made, in step 1010, the intelligent artificial speech system 170 will look up a voice file in the system speech database 172 and transfer the same to the wireless control box 121 in real-time; then, in step 1020, a conversation with the patient or user via the wireless control box 121 can be performed.

In view of the foregoing, the present disclosure starts with the caretaking of patients, focuses on the system integration technology, provides user interfaces with abundant notification/reminder functionality, allows for the prompt update of patients' physiological conditions, and facilitates nurses' comprehension of patients' current conditions.

Although various embodiments of the invention have been described above with a certain degree of particularity, or with reference to one or more individual embodiments, they are not provided to limit the scope of the present disclosure. Those with ordinary skill in the art could make numerous alterations to the disclosed embodiments without departing from the spirit or scope of this invention. Accordingly, the protected scope of the present disclosure is defined by the accompanying claims.

What is claimed is:
1. A clinical information management system, comprising:
a nurses station server;
one or more pressure sensing pads, wherein each pressure sensing pads is connected to one or more wireless control boxes configured to transmit a pressure-sensing signal to the nurses station server;
a wireless router configured to receive the pressure-sensing signal sent from the one or more wireless control boxes and configured to transmit the pressure-sensing signal to the nurses station server;

a system terminal equipment that is connected with the nurses station server and configured to receive the pressure-sensing signal uploaded by the nurses station server, wherein the nurses station server, using a system management interface based on the pressure-sensing signal, displays respective pressure distribution status of the one or more pressure sensing pads.

2. The clinical information management system of claim 1, wherein the system terminal equipment is connected to at least one selected from a group consisting of: a dual system base of the nurses station server, a hospital information system, and a cloud server.

3. The clinical information management system of claim 1, wherein:

the system terminal equipment calculates an activity status curve of a patient on a bed using the pressure distribution status, and the nurses station server uses the system management interface to display the activity status curve.

4. The clinical information management system of claim 1, wherein:

the system terminal equipment calculates the body posture and the relative position of a patient on a bed using the pressure distribution status, and the nurses station server uses the system management interface to display the body posture and the relative position.

5. The clinical information management system of claim 1, wherein, when the pressure distribution status of one pressure sensing pad of the one or more pressure sensing pads changes after the pressure distribution status remains constant for a predetermined period time and the change of the pressure distribution status exceeds a predetermined threshold value, the nurses station server uses the system management interface to transmit an awakening notification corresponding to the one pressure sensing pad.

6. The clinical information management system of claim 1, wherein:

when a path of movement of one pressure sensing pad of the one or more pressure sensing pads moves from a center towards a periphery or a corner of the one pressure sensing pad or when the one pressure sensing pad detects that a patient sits up from a corresponding bed and detects that a track of a lower part of the patient's body moves towards the periphery of the bed, the wireless control box triggers an alarm by the bedside, and the nurses station server uses the system management interface to transmit a leaving-bed warning message corresponding to the one pressure sensing pad.

7. The clinical information management system of claim 1, wherein:

when a path of movement of one pressure sensing pad of the one or more pressure sensing pads moves from a center towards a periphery or corner of the one pressure sensing pad, the wireless control box triggers an alarm by the bedside, and the nurses station server uses the system management interface to transmit a falling-off-bed attention message corresponding to the one pressure sensing pad.

8. The clinical information management system of claim 1, wherein, when one pressure sensing pad of the one or more pressure sensing pads cannot detect pressure for a predetermined period of time, the nurses station server uses the system management interface to transmit a leaving-bed notification message corresponding to the one pressure sensing pad and logs a leaving-bed time until a patient returns and is repositioned on the one pressure sensing pad.

9. The clinical information management system of claim 1, wherein:

when pressure of a portion of one pressure sensing pad of the one or more pressure sensing pads does not change after a predetermined period of time, the wireless control box triggers an alarm by a bedside, and the nurses station server uses the system management interface to transmit a pressure-reduction reminder message corresponding to the one pressure sensing pad.

10. The clinical information management system of claim 1, wherein:

when 80% to 100% of the pressure distribution of one pressure sensing pad of the one or more pressure sensing pads does not change after a predetermined period of time, the wireless control box triggers an alarm by a bedside, and the nurses station server uses the system management interface to transmit an immobilization notification corresponding to the one pressure sensing pad.

11. The clinical information management system of claim 1, wherein:

when a battery level of one pressure sensing pad of the one or more pressure sensing pads is lower than a predetermined battery level, the wireless control box triggers an alarm by the bedside, and the nurses station server uses the system management interface to transmit a low-battery message corresponding to the one pressure sensing pad.

12. The clinical information management system of claim 1, wherein, when the nurses station server does not receive the pressure-sensing signal of the wireless control box of one pressure sensing pad of the one or more pressure sensing pads via the wireless router after a predetermined period of time, the nurses station server uses the system management interface to transmit a signal-interrupted message corresponding to the one pressure sensing pad.

13. The clinical information management system of claim 1, wherein:

when the wireless control box detects that one pressure sensing pad of the one or more pressure sensing pads is removed or has a loose contact, the wireless control box triggers a pressure-sensing-pad-removed-or-loose-contact message to the nurses station server and triggers an alarm by a bedside, the nurses station server uses the system management interface to transmit a pressure-sensing-pad-removed or inadequate-contact signal corresponding to the one pressure sensing pad.

14. The clinical information management system of claim 1, wherein:

when the pressure sensing pads and the wireless control box are connected, the wireless control box determines a size or type of the one or more pressure sensing pads and the nurses station server uses the system management interface to display the size and type corresponding to the one or more pressure sensing pads.

15. The clinical information management system of claim 14, wherein, when the nurses station server, during a period of time, receives more than a predetermined number times of delay in the pressure-sensing signal from one pressure sensing pad of the one or more pressure sensing pads via the wireless router, one or more mobile devices use a mobile user interface to transmit a signal-interrupted message corresponding to the one pressure sensing pad.

16. The clinical information management system of claim 1, wherein, when the system terminal equipment or the nurses station server obtains a patient-bed-transfer notification via a hospital information system, or when the system terminal equipment or the nurses station server automatically detects a patient-repeated-admission information, the nurses station server uses a system management interface to transmit a bed-transfer-confirmation message corresponding to the one pressure sensing pad.

17. The clinical information management system of claim 1, wherein, when the system terminal equipment or the nurses station server obtains a patient-bed-transfer information via a hospital information system, or when the system terminal equipment or the nurses station server automatically detects a patient-repeated-admission information, the nurses station server uses a system management interface to present a bed-transfer-confirmation message corresponding to the one pressure sensing pad.

18. The clinical information management system of claim 1, wherein, when the system terminal equipment or the nurses station server obtains a patient-discharge information via a hospital information system, or after a patient leaves the corresponding bed for a predetermined period of time and the system terminal equipment or the nurses station server detects that the corresponding pressure sensing pad has been removed, the nurses station server uses a system management interface to transmit a corresponding discharge-confirmation message.

19. The clinical information management system of claim 1, wherein, when the system terminal equipment or the nurses station server obtains a patient-discharge information via a hospital information system, or after a patient leaves a corresponding bed for a predetermined period of time and the system terminal equipment or the nurses station server detects that a corresponding pressure sensing pad has been removed, the nurses station server uses a system management interface to transmit a corresponding discharge-confirmation message.

20. The clinical information management system of claim 1, wherein, when the system terminal equipment or the nurses station server obtains a patient-discharge information via a hospital information system, or after a patient leaves a corresponding bed for a predetermined period of time and the system terminal equipment or the nurses station server detects that a corresponding pressure sensing pad has been removed, the nurses station server uses a system management interface to transmit a corresponding discharge-confirmation message.

21. The clinical information management system of claim 1, wherein, when the wireless control box triggers an alarm signal, a system management interface of the nurses station server is configured to enable a health-care professional to conduct a conversation with a patient.

22. The clinical information management system of claim 1, further comprising:
an intelligent artificial speech system that is configured to transfer a voice file to the wireless control box in real-time and conduct a conversation with a patient via the wireless control box when the system terminal equipment or the nurses station server detects an alarm signal.

23. The clinical information management system of claim 1, wherein data is encrypted and a data transmission verification is performed when the data is transmitted and received among the wireless control box, the wireless router, and the nurses station server, and when a system management interface of the nurses station server stores the data in the system terminal equipment.

24. The clinical information management system of claim 1, wherein, when the nurses station server, during a period of time, receives more than a predetermined number times of delay in the pressure-sensing signal from one pressure sensing pad of the one or more pressure sensing pads via the wireless router, the nurses station server uses a system management interface to transmit a low-transmission-quality message corresponding to the one pressure sensing pad.

25. The clinical information management system of claim 1, wherein, when a variation of the pressure-sensing signal of one pressure sensing pad of the one or more pressure sensing pads is maintained at a fixed value for a predetermined period of time, the nurses station server uses a system management interface to transmit a patient-convulsion notification.

26. The clinical information management system of claim 1, wherein, when the pressure-sensing signal of one pressure sensing pad of the one or more pressure sensing pads is converted to a patient-body-weight basis, and when a body weight varies outside either an upper-limit or a lower-limit value, the nurses station server uses a system management interface to transmit a patient-body-weight-variation notification.

27. The clinical information management system of claim 1, wherein, when the pressure-sensing signal of one pressure sensing pad of the one or more pressure sensing pads generates a variation at a fixed frequency, the nurses station server is configured to detect a patient's numbers of breath and heartbeat, and when the patient's numbers of breath and heartbeat register outside either an upper-limit or a lower-limit value, the nurses station server uses a system management interface to transmit a patient-breath-or-heartbeat-abnormal notification.

28. The clinical information management system of claim 1, wherein:
the nurses station server provides a healthcare professor with a platform for inputting or updating a patient-fall-risk assessment and a bedsore-risk assessment,
the nurses station server monitors a bedridden patient's activity status in real-time and connects with a hospital information system to obtain a patient-medication status and
a system management interface displays a patient-fall-risk index and a bedsore-risk index that is derived from the bedridden patient's activity status and the patient-medication status.

29. A clinical information management system, comprising:
a nurses station server;
one or more pressure sensing pads, wherein each pressure sensing pads is connected to one or more wireless control boxes configured to transmit a pressure-sensing signal to the nurses station server;
a wireless router, configured to receive the pressure-sensing signal sent from the one or more wireless control boxes and configured to transmit the pressure-sensing signal to the nurses station server;
a system terminal equipment that is connected with the nurses station server and configured to receive the pressure-sensing signal uploaded by the nurses station server,
one or more mobile devices, configured to receive messages from the nurses station server based on the status of the pressure sensing signal,
wherein the one or more mobile devices, using a mobile user interface, display respective pressure distribution status of the one or more pressure sensing pads.

30. The clinical information management system of claim 29, wherein the mobile device is at least one selected from a group consisting of: a medical rounds cart, a hand-held mobile device, and a wearable device.

31. The clinical information management system of claim 29, wherein the nurses station server, using the distribution status, display body posture and body position information for each of the one or more pressure sensing pads.

* * * * *